United States Patent [19]

Acker et al.

[11] Patent Number: 5,006,119
[45] Date of Patent: Apr. 9, 1991

[54] HOLLOW CORE COAXIAL CATHETER

[75] Inventors: Loren C. Acker; Daniel C. Harmony, both of Tucson, Ariz.

[73] Assignee: Engineering & Research Associates, Inc., Tucson, Ariz.

[21] Appl. No.: 357,058

[22] Filed: May 25, 1989

[51] Int. Cl.$^5$ .............................................. A61B 17/36
[52] U.S. Cl. ........................................ 606/27; 606/28; 606/32; 604/96
[58] Field of Search ................. 604/95, 96; 606/7, 15, 606/16, 27–29, 33, 45, 49, 159, 194; 128/660.03, 662.06, 804, 784, 786; 174/28, 47

[56] References Cited

U.S. PATENT DOCUMENTS

| 4,641,649 | 2/1987 | Walinsky et al. | 128/804 X |
|---|---|---|---|
| 4,643,186 | 2/1987 | Rosen et al. | 606/33 |
| 4,709,698 | 12/1987 | Johnston et al. | 606/31 X |
| 4,754,752 | 7/1988 | Ginsburg et al. | 606/27 |
| 4,799,479 | 1/1989 | Spears | 606/7 |
| 4,808,164 | 2/1989 | Hess | 606/7 X |

Primary Examiner—Robert A. Hafer
Assistant Examiner—Kerry Owens
Attorney, Agent, or Firm—Cahill, Sutton & Thomas

[57] ABSTRACT

A hollow core coaxial catheter supporting a heatable probe or balloon transmits electrical power, such as RF energy, to the ohmically resistive probe or balloon. The hollow core may accommodate passage of a guide wire, fiber optics for imaging or laser, fluid flow for perfusion and/or a lumen for fluid inflation and pressurization of a balloon. Inner and outer electrical conductors are disposed on radially opposed sides of dielectric tubing with an outer covering of dielectric material mechanically shielding and electrically insulating the outer conductor. A similar inner covering of dielectric material may be disposed radially inwardly of the inner conductor to mechanically and electrically insulate the inner conductor. An ohmically resistive load, in the event RF energy is the power source, interconnects the inner and outer conductors to form the probe. An inflatable balloon of predetermined expanded configuration and inflatable via the lumen may be formed proximate or as a part of the probe to expand arterial plaque heated by the probe or to heat and expand the arterial plaque to a predetermined configuration. The RF energy, if used, will heat the probe or balloon and monitor and manage the temperature of the probe or the balloon.

62 Claims, 3 Drawing Sheets

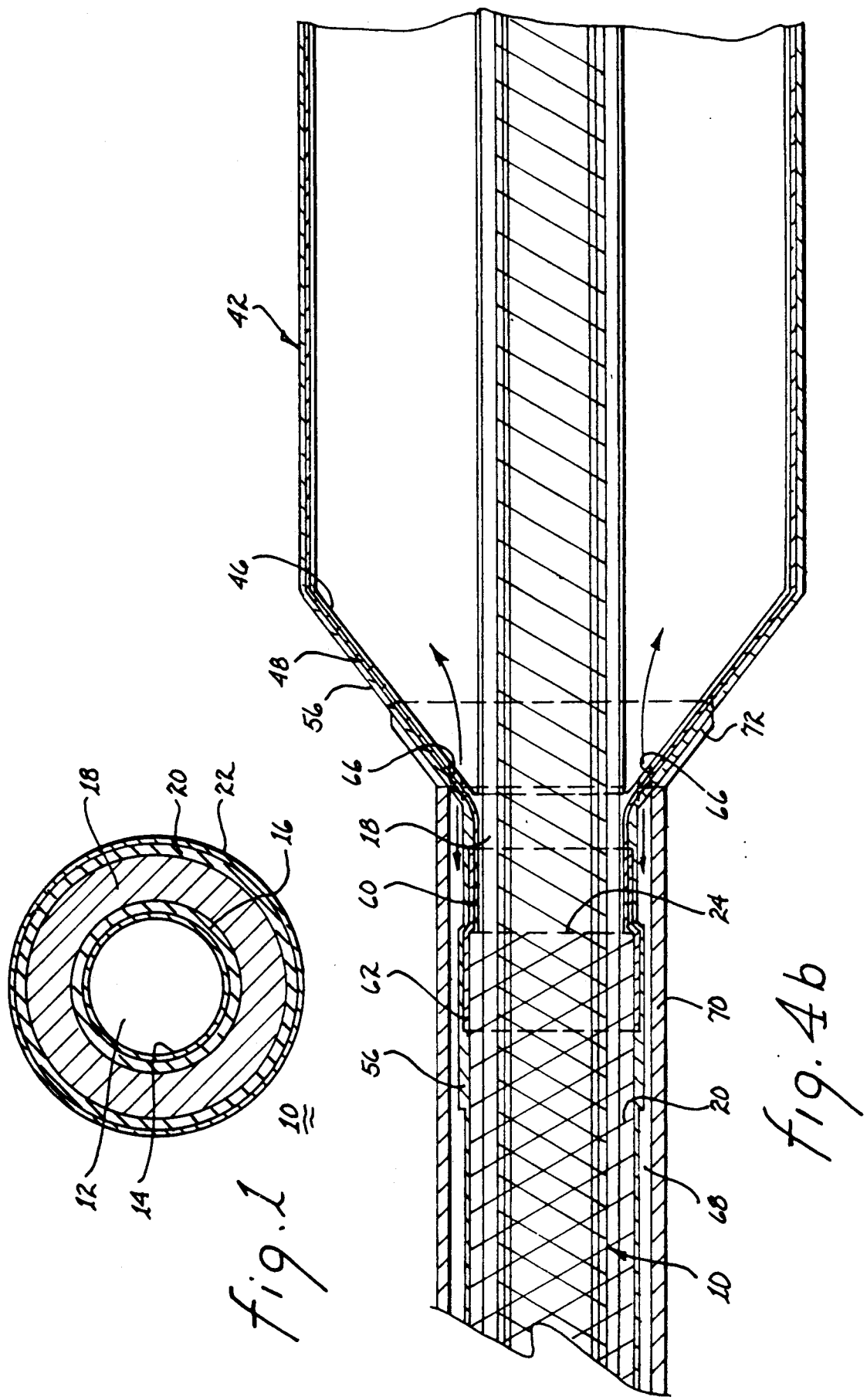

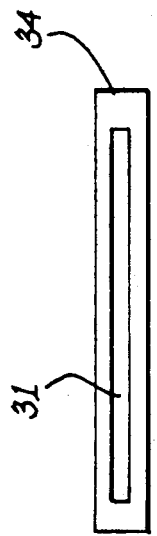
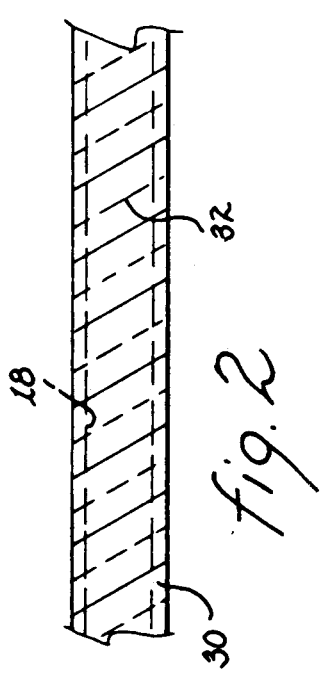
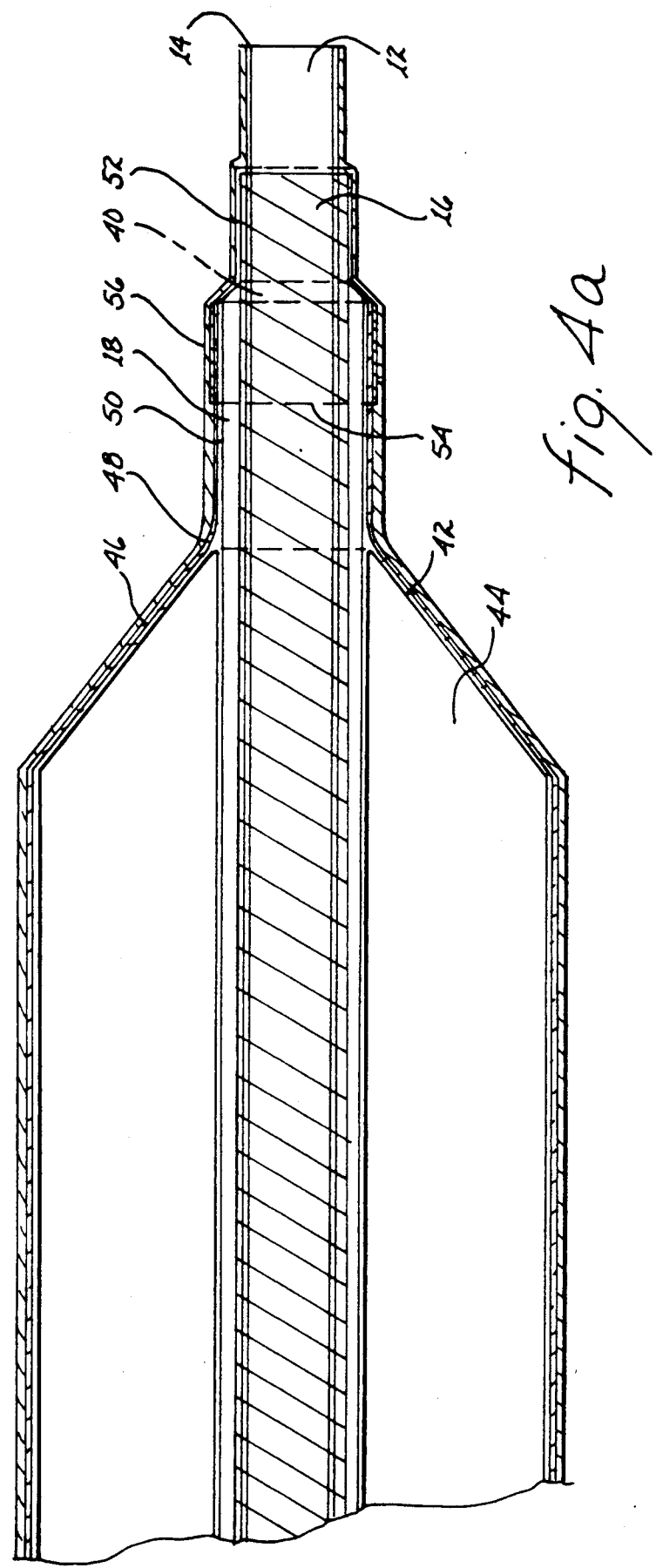

HOLLOW CORE COAXIAL CATHETER

RELATED PATENT APPLICATIONS

The present application describes an invention related to the subject matter described in a copending patent application entitled "RF ENERGIZED AND TEMPERATURE MONITORED AND MANAGED CATHETER MOUNTED PROBE", assigned Ser. No. 337,903, filed on Apr. 13, 1989, and assigned to the present Assignee.

BACKGROUND OF THE INVENTION

1. Field of the Invention

The present invention relates to revascularization of coronary and peripheral arteries through catheter apparatus for treating coronary stenosis and for reestablishing and maintaining coronary circulation and, more particularly, to a highly flexible hollow core coaxial cable for supporting and energizing an electrically or radiant energy heated probe or balloon or fluid inflated balloon, while simultaneously maintaining blood flow and fiber optics provisions.

2. Description of the Prior Art

Cardiovascular restriction or occlusion due to coronary artery disease and peripheral vascular disease may be addressed by any of a number of medical procedures. Pharmacological approaches for inducing dilation of the blood vessels are of a temporary nature and may have undesirable secondary results. Surgical techniques include coronary bypass surgery involving implantation of substitute blood vessels to bypass blood flow around the blockage; as with any major surgery, substantial risks are involved. Recent improvements in laser technology have resulted in development of the capability to medically insert a laser delivery fiber optic close to the blockage to permit lasing the blockage. Such lasing may vaporize, segment or otherwise disengage plaque from the artery. An inflatable balloon may be used to maintain the laser emitting fiber optic end close to the blockage and to widen the artery. Such coronary laser angioplasty procedures and equipment suffer from several significant drawbacks. The particulate matter disengaged will become suspended in the blood stream and may become relocated elsewhere. The extraordinarily high and uncontrolled heat from the laser beam or laser heated tip may permanently damage the artery wall or nearby tissue. The disposable and non disposable parts of the apparatus are very expensive. Danger also exists from laser perforation of the blood vessel wall.

Radio frequency (RF) energy has been discharged from the discharge end of a catheter to electro abrade arterial plaque. The lack of control of the amount of energy radiated poses a serious threat to cardiovascular integrity and to damage of even surrounding tissue. Alternatively, RF has been used to heat the tip of a catheter, which heated catheter is used to thermally mold and displace the plaque. To be effective, sufficient power must be applied to overcome the damping effects of blood flow rate, the distance between the source of RF radiation or hot tip and the plaque, the thickness of the plaque, the extent of fatty tissue, etc.; where these damping factors are minimal, cardiovascular damage is probable. Alternatively, a two electrode device for transmitting RF (discharging) energy therebetween has been used at a specific location adjacent one of the electrodes. The high uncontrolled concentration of heat poses a serious threat of cardiovascular damage.

Ultrasonic techniques have been used to emulsify or fragment arterial plaque. In conjunction therewith, an aspiration tube may be employed to remove the fragmented plaque.

Recent techniques suggest the use of heating liquids adjacent arterial plaque by a chemical exothermic reaction.

SUMMARY OF THE INVENTION

A highly flexible hollow core coaxial catheter includes electrical conductors disposed on the inner and outer surfaces of flexible dielectric tubing. An inner sheath is interiorly juxtaposed with the inner conductor to shield it against mechanical abuse and to provide electrical insulation. An outer dielectric shield encircles the outer conductor to shield it against abuse and to electrically insulate it. An electrical ohmically resistive load interconnects the inner and outer conductors at the distal end of the catheter in response to current flow through the conductors from a source of electrical energy. The source of electrical energy may be an RF generator, including monitoring and managing circuitry for regulating the applied RF energy to maintain the ohmically resistive load at a predetermined and adjustable temperature. A hollow expandable balloon, connected to a source of fluid, may be disposed at the distal end of the catheter. The hollow balloon defines a predetermined configuration in its expanded state to accommodate molding of heated arterial plaque into a predetermined configuration. In one embodiment of the expanded balloon, an ohmically resistive load electrically interconnected between the inner and outer conductors of the hollow coaxial catheter is disposed upon the balloon to heat the arterial plaque to a predetermined temperature simultaneously with application of an expansion force to mold the heated arterial plaque to a configuration predetermined by the shape of the expanded balloon. Aside from accommodating the presence of a lumen to inflate the balloon, the hollow core of the catheter may support a guide wire for insertion and manipulation of the catheter within the vascular system. Furthermore, the hollow core catheter may be used for the purpose of accommodating blood flow during an angioplasty procedure. Furthermore, the hollow core catheter may be used for insertion of fiber optics, for optical image monitoring the procedure or for additional heating from a laser source.

It is therefore a primary object of the present invention to provide a highly flexible hollow core coaxial catheter for transmitting electrical power to a heatable probe.

Another object of the present invention is to provide a hollow core coaxial catheter for guiding and housing the catheter over a guide wire while transmitting electrical power to a probe.

Yet another object of the present invention is to provide a hollow core coaxial catheter for housing a lumen to fluid inflate a balloon while transmitting electrical power to heat an element associated with the balloon.

Still another object of the present invention is to provide a hollow core coaxial catheter for transmitting electrical power to an ohmically resistive load disposed intermediate the conductors at the distal end of the catheter.

A further object of the present invention is to provide and heat an inflatable balloon disposed at the distal end of a hollow core coaxial catheter, which catheter transmits RF energy to an ohmically resistive load associated with heating the balloon.

A yet further object of the present invention is to provide a hollow core coaxial catheter for supporting at the distal end an inflatable balloon of predetermined inflated configuration to conform encircling arterial plaque with such configuration upon heating of the balloon with RF energy transmitted through the conductors of the coaxial catheter.

A still further object of the present invention is to provide an inflatable balloon of predetermined inflated configuration mounted at the distal end of a hollow core coaxial catheter which catheter transmits electrical power to a heat responsive load associated with the balloon and directs fluid into and out of the balloon from a lumen while accommodating a guide wire disposed within the hollow core to position the catheter pre and post an angioplasty procedure.

A still further object of the present invention is to provide an RF energy responsive probe mounted at the distal end of a hollow core coaxial catheter.

A still further object of the present invention is to provide a hollow core coaxial catheter for transmitting RF energy to an RF responsive inflatable balloon disposed at the distal end.

A still further object of the present invention is to provide a method for applying heat to arterial plaque and for simultaneously expanding the arterial plaque during an angioplasty procedure.

A still further object of the present invention is to provide a method for radially heating and expanding arterial plaque during an angioplasty procedure by application of RF energy transmitted through a hollow core coaxial conductor.

A still further object of the present invention is to provide a method for transmitting electrical energy through a catheter.

A still further object of the present invention is to provide a method for transmitting RF energy though a catheter during an angioplasty procedure.

A still further object of the present invention is to provide a hollow core coaxial catheter for accommodating transmission of electrical power to heat a probe, transmitting probe temperature monitoring signals and heating the probe.

A still further object of the present invention is to provide a method using a hollow core coaxial catheter for transmitting electrical power and control signals, accommodating fluid flow to an inflatable balloon, supporting a guide wire and permitting continuing blood flow during an angioplasty procedure.

It is a still further object of the present invention to provide a method for transmitting power, transmitting control and monitoring signals, transmitting fluid for actuating an inflatable balloon, supporting a guide wire and accommodating blood flow during an angioplasty procedure involving heating and radial expansion of arterial plaque.

These and other objects of the present invention will become apparent to those skilled in the art as the description thereof proceeds.

BRIEF DESCRIPTION OF THE DRAWINGS

The present invention will be described with greater clarity and specificity with reference to the following drawings, in which:

FIG. 1 illustrates a cross section of a hollow core coaxial catheter;

FIG. 2 illustrates a wrapped electrical conductor to ensure high flexibility of the coaxial cable, FIG. 3 illustrates a cross section of an insulated ribbon conductor;

FIGS. 4A and 4B illustrate cross sectional views of a flexible hollow core coaxial catheter supported inflatable balloon for transmitting electrical power, transmitting monitoring signals, supporting a guide wire and accommodating a lumen for inflating and deflating the balloon;

DESCRIPTION OF THE PREFERRED EMBODIMENT

Figure 5:
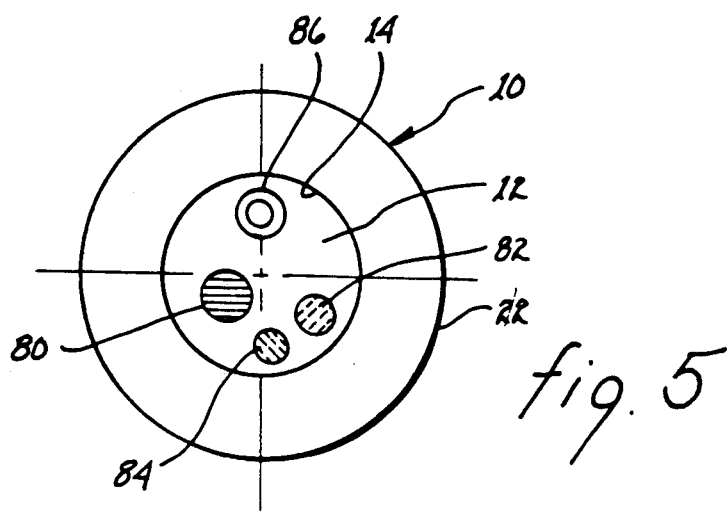
FIG. 5 is a cross sectional view of the catheter and illustrating various elements locatable within the bore of the catheter.

Catheters useful in heat assisted angioplasty procedures must meet three basic parameters. There must be a source of energy to effect heating; because of the potential hazard of an electrical energy source, a low voltage direct current source is preferable. Such source, if a battery, also provides the freedom of portability. A second parameter relates to the transmission media for transmitting the energy from the source to the remote point of application. Because the energy source is preferably low voltage, low current, the transmission media must satisfy certain electrical parameters to avoid preventable losses. As an example, wires of extremely small diameter have electric resistance of sufficient magnitude to generate heat even when conducting small electrical currents. Furthermore, the resistance of the wires will present a voltage drop as a function of Ohm's Law. Preferably, a coaxial cable (coax) should be used for transmitting RF energy to avoid losses from and the effects of spurious radiation along the transmission media. The third parameter relates to the load for receiving the transmitted energy and converting the energy to heat. Preferably, the load is configured or configurable to be capable of molding the heated arterial plaque to a predetermined configuration to open and maintain open the artery after cooling of the arterial plaque. Because the catheter is inserted within a blood vessel and advanced therealong to the location of a restriction or an occlusion, cross sectional size must be at a minimum while providing the capability for flexing and bending to accommodate the normally tortuous path to the restriction or occlusion.

Where an inflatable balloon is used in conjunction with a heatable probe or as the heatable probe, means are formed or disposed within the catheter to permit fluid flow to and from the balloon for inflation and deflation purposes. To assist in manipulating and advancing the catheter, a guide wire extends through and protrudes beyond the distal end of the catheter. Real time diagnostic imaging can be accomplished by locating within the hollow core fiber optic elements necessary to illuminate and view the vascular site. Preferred procedures suggest the necessity of maintaining blood flow, rather than blood blockage, at the site of an angioplasty procedure. Such flow or perfusion can be accommodated by channeling the blood flow through the hollow core of the catheter.

To provide an overview of the power source for heating the load, whether disposed as a probe at the distal end of the catheter or as an inflatable balloon at the distal end of the catheter, certain considerations attendant transmission of the radio frequency (RF) energy through the catheter will be discussed. The RF energy is generated by an energy source, such as that described in the above referenced application, Ser. No. 337,903, and transmitted via the catheter to the probe or balloon. The electrical resistance of the load at the probe or balloon will change as a function of temperature. By measuring this resistance change, it is possible to determine the temperature or to correlate the temperature with a change in resistance. By providing a constant current source for a DC current or low frequency AC current (multiplexed or filtered to segregate it from the RF generator), a change in electrical resistance of the load will produce a voltage responsive to the change in resistance. This voltage change can be sensed and the change is used to regulate the power of the RF energy applied to the load. Because the electrical resistance of the load must be extremely low, the transmission media through the catheter may have a significant effect upon the overall resistance. Moreover, the resistance of the transmission media will produce heat. It is therefore of significant import to employ electrical conductors within the catheter which are compatible with transmission of RF energy and which provide a low resistive path relative to the load. By using the below described coaxial conductors, spurious RF radiation along the catheter will be minimized and the resistance of the conductors will be sufficiently low to avoid heat generation and a voltage drop of any significance along the catheter.

Because of the small physical size constraints imposed upon the probe, the balloon and catheter to permit them to be inserted within and advanced through an affected section of the cardiovascular system having a restriction or an occlusion, flexible components very small in diameter must be used. Where the catheter must perform multiple functions, it is mandatory that one or more elements be capable of performing more than one function in order to meet the preferred size constraints. Preferably, the overall diameter of the catheter is on the order of 0.025 to 0.030 inches and it will readily negotiate 0.5 inch radius turns.

Referring to FIG. 1, there is illustrated a hollow core coaxial catheter 10. The hollow center or core 12 is approximately 0.020 inches in diameter. An inner cylindrical layer 14 mechanically defines core 12; it is of dielectric material to provide electrical insulation. Preferably, inner layer 14 is of polyimide or PTFE; the former is sold under the trademark Kapton by the Dupont company and the latter is sold under the trademark Teflon by the Dupont company. The wall thickness of inner insulative layer 14 may be in the range of 0.5 to 1.0 mils. An inner conductor 16, which may be of copper, generally defines a cylindrical shape concentric with inner layer 14. The thickness of the inner conductor may be in the range of 0.5 to 2.0 mils. A cylinder 18 is disposed radially outwardly concentric with inner conductor 16. The cylinder is of dielectric material, such as polyimide or PTFE. The wall thickness of cylinder 18 may be in the range 4.0 to 10.0 mils. An outer conductor 20, which may be of copper, is disposed about cylinder 18. It may have a wall thickness in the range of 0.5 to 2.0 mils.

Layer 14 and cylinder 18 are illustrated as circular in cross section; such configuration is not mandatory and other cross sectional configurations can be employed. The dielectric material of either or both of layer 14 and cylinder 18, in addition to the above noted materials, may be a glass ceramic compound or an alumina silica compound of the type available from Galileo Electro-Optics Corp. of Sturbridge, Mass. These compounds, used in the configuration and sizes discussed below, have a flexural modulus which permits the below described flexibility and bending radius.

As RF energy is transmitted through the inner and outer conductors, it is necessary that the wall thickness of cylinder 18 be sufficient to minimize losses between the conductors. Accordingly, both the power levels and the frequency of the RF energy will impose certain constraints upon the wall thickness of cylinder 18. A outer layer 22 encapsulates outer conductor 20 to electrically insulate it and to physically shield it against abuse and damage.

The preferred use of polyimide material is based upon certain of the properties of the material. It has high dielectric properties whereby the distance between the electrical conductors can be reduced without fear of voltage breakdown as compared to other materials. It can be heated to a relatively high temperature without melting, deformation or other damage; typically, it will withstand continuous heat of over 250° C. and heat up to 500° C. for short periods of time. It has certain structural, torsional and flexural properties which are beneficial. It has great tensile strength and is relatively inelastic.

In one embodiment, the inner and outer conductors may be deposited upon the corresponding surfaces of cylinder 18. Such deposition could fracture and produce open circuits in the event the underlying material expands/contracts in response to the stresses and strains imposed. The deposited material may be fine grain or pure copper to assure maximum flexibility and elasticity. Because one of the properties of polyimide is that of relative inelasticity, expansion will not occur and fracturing of the deposited conductors is unlikely to occur.

Referring jointly to FIGS. 2 and 3, there is shown an alternate configuration of the inner and/or outer conductors (16,20). By wrapping cylinder 18 with a thin strip of conductive material (30), such as copper, the coax becomes highly flexible and the possibility of fracturing a deposition applied conductor will be eliminated. Such wrapping will also augment the structural integrity of the catheter. Moreover, inner conductor 16 can be similarly wrapped within cylinder 18; such wrapping may be within the interior surface of the cylinder or about inner layer 14. In the latter configuration, cylinder 18 may be formed about layer 14 wrapped by conductor 16 or slid thereonto.

Referring to FIG. 2, there is shown a ribbon conductor 30 wrapped about the exterior surface of cylinder 18. As depicted by dashed lines 32, the strip conductor may be overlapped by 50% to provide a double thickness for continuous electrical conduction and shielding and an essentially smooth exterior and interior surface.

FIG. 3 illustrates, in representative form, a copper strip conductor 30. This conductor may be on the order of 0.250 inches wide and 0.0013 inches thick. Where dictated by manufacturing and/or operational requirements, strip 30 may be encapsulated polyimide ribbon 31 within copper coating 34.

Referring to FIGS. 4A and 4B, there is shown an inflatable balloon 42 secured to the distal end of a hollow core coaxial catheter 10. The following detailed description of the structural considerations attendant the coaxial catheter and the balloon will be commenced generally from the distal end. Core 12 of catheter 10 is defined by the protruding part of inner layer 14. Inner conductor 16, which is depicted as a wrap of a ribbon of conductive material terminates short of the distal end. This conductor may be dimensioned as discussed with respect to FIGS. 2 and 3 or it may be in the manner of a flat wire 20 mils wide and 1 mil thick which has been double wrapped to provide a 2 mil thickness. Cylinder 18, being distally beveled by bevel 40, as shown, terminates proximally of the end of inner conductor 16. An annular balloon 42 defining an inflatable annular cavity 44 is supported by and disposed about the exposed length of cylinder 18. Exterior surface 46 of the balloon is coated or electro deposited with a coat 48 of ohmically resistive material that serves as a heatable load thermally responsive to application of RF energy. The distal end of balloon 42 includes an annular section 50 circumscribing cylinder 18 and extending distally from cavity 44 to approximately the terminal end of cylinder 18. An electro deposited layer 52 of electrically conductive material extends from about the exposed portion of conductor 16 along bevel 40 and about a proximal segment of the exposed area of cylinder 18. A ring 54 of electrically conductive material electrically interconnects substrate 52 with electrically conductive coat 48. Accordingly, conductor 16 is electrically connected to coat 48. A covering 56 of electrically insulating material is disposed about catheter 10 distally of balloon 42 and about the balloon. This covering electrically insulates the electrical elements attendant the distal end of the catheter and the balloon. Moreover, the covering serves a structural function of maintaining the electrical conductors in their respective positions and prevents slippage between the balloon and the encircled catheter.

The following description will relate primarily to the structure attendant the proximal end of balloon 42. Outer conductor 20 terminates at end 24 distally of the balloon. Surface 46 of balloon 42 extends proximally to form an annular section 60 in circumscribing relationship with cylinder 18. The proximal end of the annular section may abut end 24, as shown. Coat 48 of electrically conductive material and disposed upon exterior surface 46 extends to and circumscribes annular section 60. A ring 62 of electrically conductive material overlies and is in electrical contact with the distal end of outer conductor 20 and the proximal end of coat 42. Thereby, an electrical path is established between outer conductor 20 and coat 48 disposed about balloon 42.

Covering 56 extends proximally from balloon 42 and encloses annular section 60 and ring 62. The covering may extend proximally along catheter 10 to physically protect and electrically shield outer conductor 20.

From the above description, it will become apparent that coat 48 of electrically conductive material forms a load interconnected between outer conductor 20 and inner conductor 16. This coat, if made of ohmically resistive material, may be heated upon application of RF energy transmitted via the inner and outer conductors.

Inflation and deflation of balloon 42 may be accomplished by a lumen disposed within core 12 and extending into cavity 44 of the balloon. Such extension into the cavity may be effected by penetration of inner layer 14, inner conductor 16 and cylinder 18. Alternatively, and as illustrated in FIG. 4B, a plurality of passageways 66 may be formed at the proximal end of balloon 42 through covering 56, coat 48 and exterior surface 46. These passageways are in fluid communication with an annular cavity 68 disposed about catheter 10. The annular cavity may be developed by a sheath 70 concentric with the catheter. A flared or cone section 72 of the sheath may be employed to sealingly engage the proximal end of balloon 42, as illustrated. Necessarily, the junction between the cone section and the balloon must be sealed and remain sealed during both inflation and deflation of the balloon.

To provide perspective to the size of catheter 10 and balloon 42, representative dimensions of the various components, shown in FIGS. 4A and 4B, are listed below.

Core 12 - 20 mils diameter
Layer 14 - 0.5 to 2 mils thick
Inner conductor 16 - 0.1 to 2 mils thick
Cylinder 18 - 6 to 10 mils thick
Outer conductor 20 - 0.1 to 2 mils thick
Rings 54,62—0.5 mils thick
Covering 56 - 0.3 to 2 mils thick
Surface 46 - 0.5 mils thick
Ohmically resistive coat 48 - 500 Å to 2 mils thick
Sheath 70 - 1 to 3 mils thick To enlarge the scope of utility of the catheter for use in angioplasty procedures, it is preferrable that the catheter be not only very flexible but also small in cross sectional area. The dimensions of the various components listed above permit fabrication of a catheter having a cross section of not more than 0.0030 square inches. Through judicious selection of component dimensions, the cross sectional area can be less than 0.0020 square inches.

The expanded size and configuration of balloon 42 will vary as a function of the medical procedure to be performed; its selection is made by the physician.

Referring to FIG. 5, core 14 of catheter 10 may be employed to house several elements useful in the analysis, performance and evaluation of an angioplasty procedure. A guide wire 80 is disposed within the catheter and extends from the distal end of the catheter. Such a guide wire is manipulatable by a physician to thread the distal end of the catheter to a particular vascular site where the angioplasty procedure is to be performed. To assist in evaluating and diagnosing a vascular site, as well as other physiological conditions, a fiber optic element 82 may be disposed within the hollow core and protrude from the distal end. As is well known, such fiber optic element is capable of imaging a site of interest. To provide visible light, for illuminating a site of interest for imaging purposes, a source of light 84 may be housed within core 14 to illuminate the site of interest proximate the distal end of the catheter. A lumen 86 may also be disposed within hollow core 14 to serve as a conduit for fluid flowing into and out of balloon 42.

Figure 6:
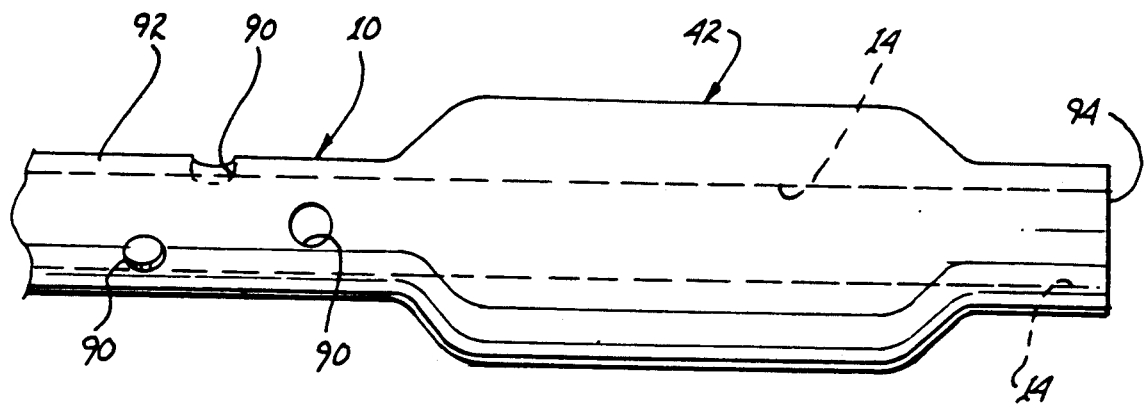
FIG. 6 is a side view of the distal end of the catheter and showing apertures for accommodating perfusion.

During certain angioplasty procedures and for other reasons, it would be preferable not to impede blood flow during an angioplasty procedure at a vascular site. As shown in FIG. 6, hollow core 14 can accommodate such perfusion. A plurality of apertures 90 extend through wall 92 of catheter 10. These apertures will have minimal disruptive effect upon the RF energy transmitted through conductors 16 and 20. Apertures 90, in combination with opening 94 defined by hollow core 14 at the distal end of the catheter, accommodate perfusion through core 14 past the interior of balloon 42. Accordingly, catheter 10 can accommodate perfusion during inflation of the balloon.

Figure 7:
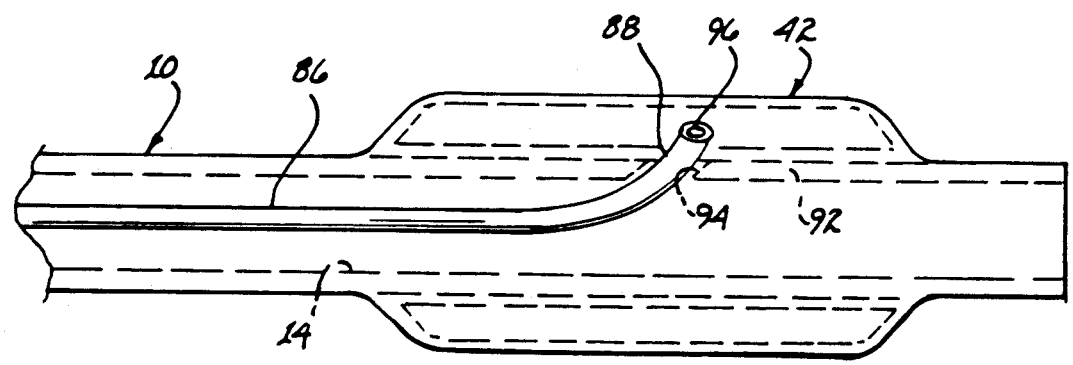
FIG. 7 is a side view of the distal end of the catheter illustrating a variant for inflating and deflating the balloon.

As shown in FIG. 7, balloon 42 may be inflated and deflated by flow of fluid through lumen 86. The lumen is generally housed within hollow core 14. The proximal end of the lumen must necessarily be connected to a source of fluid for controlling the amount, rate and direction of fluid flow. Generally, the lumen and balloon are under pressure from a source of fluid under pressure and the pressure is adjusted for inflation and deflation. Terminal end 88 of the lumen is penetrably engaged with wall 92 via a passageway 94. Preferably, the lumen is in sealed engagement with the passageway. Terminal end 88 terminates within the envelope defined by balloon 42 and includes an opening 96 to establish fluid communication between the interior of the balloon and the lumen.

It is to be understood that certain or all of the optic related and hydraulic conduits may be integrated within the inner and outer surfaces of cylinder 18.

While the principles of the invention have now been made clear in an illustrative embodiment, there will be immediately obvious to those skilled in the art many modifications of structure, arrangement, proportions, elements, materials and components used in the practice of the invention which are particularly adapted for specific environments and operating requirements without departing from those principles.

We claim:

1. A flexible hollow core coaxial catheter usable in angioplasty procedures for transmitting electrical energy, said catheter comprising in combination:
   (a) a flexible hollow member defining a passageway extending therewithin and having an inner surface and an outer surface;
   (b) a first electrical conductor juxtaposed with the inner surface, said first conductor maintaining a substantial part of the cross sectional area of the passageway unoccupied;
   (c) a second electrical conductor juxtaposed with the outer surface;
   (d) first means for electrically insulating said first electrical conductor within the passageway;
   (e) second means for electrically insulating said second electrical conductor about said hollow member;
   (f) a load supported by said hollow member and responsive to application of electrical energy for heating arterial plaque during the angioplasty procedure; and
   (g) means for electrically interconnecting said first and second electrical conductors with said load.

2. The flexible hollow core coaxial catheter as set forth in claim 1 wherein said first electrical conductor is deposited on the inner surface.

3. The flexible hollow core coaxial catheter as set forth in claim 1 wherein said second electrical conductor is deposited on the outer surface.

4. The flexible hollow core coaxial catheter as set forth in claim 3 wherein said first electrical conductor is deposited on the inner surface.

5. The flexible hollow core coaxial catheter as set forth in claim 1 wherein said second conductor is wrapped about the outer surface.

6. The flexible hollow core coaxial catheter as set forth in claim 1 wherein said first conductor is wrapped adjacent the inner surface.

7. The flexible hollow core coaxial catheter as set forth in claim 1 including an inner layer of dielectric material disposed within the passageway and radially inwardly of said first electrical conductor.

8. The flexible hollow core coaxial catheter as set forth in claim 7 wherein said inner layer includes an exterior surface and wherein said first conductor is disposed about the exterior surface of said inner layer.

9. The flexible hollow core coaxial catheter as set forth in claim 8 wherein said first electrical conductor is wrapped about the surface of said inner layer.

10. The flexible hollow core coaxial catheter as set forth in claim 9 wherein said inner layer is cylindrical.

11. The flexible hollow core coaxial catheter as set forth in claim 10 wherein said hollow member is cylindrical.

12. The flexible hollow core coaxial catheter as set forth in claim 1 wherein said hollow member is cylindrical.

13. The flexible hollow core coaxial catheter as set forth in claim 1 including a guide wire housed within said passageway for guiding said catheter during the angioplasty procedure.

14. The flexible hollow core coaxial catheter as set forth in claim 1 including means for imaging the vascular site, said imaging means being housed within said passageway.

15. The flexible hollow core coaxial catheter as set forth in claim 14 wherein said imaging means comprises a fiber optic and means for illuminating the area to be imaged.

16. The flexible hollow core coaxial catheter as set forth in claim 1 including a balloon for expanding the vascular site at which an angioplasty procedure is to be performed and a lumen is disposed within said passageway in fluid communication with said balloon for inflating and deflating said balloon.

17. The flexible hollow core coaxial catheter as set forth in claim 16 wherein said lumen penetrates a wall of said hollow member between said passageway and said balloon.

18. A flexible hollow core coaxial catheter for transmitting RF energy from a source of RF energy to an arterial plaque heating probe, said catheter comprising in combination:
   (a) a first electrical conductor for conducting RF energy;
   (b) a bore disposed radially inwardly of said first conductor;
   (c) a second electrical conductor disposed outside of said bore for conducting RF energy;
   (d) a dielectric member disposed intermediate said first and second conductors for impeding flow of RF energy between said first and second conductors; and
   (e) means for electrically interconnecting the probe between said first and second conductors to heat the probe upon transmission of RF energy from the source of RF energy through said first and second conductors to the probe.

19. The flexible hollow core coaxial catheter as set forth in claim 18 wherein said first conductor circumscribes said bore.

20. The flexible hollow core coaxial catheter as set forth in claim 19 wherein said dielectric member circumscribes said first conductor.

21. The flexible hollow core coaxial catheter as set forth in claim 20 wherein said second conductor circumscribes said dielectric member.

22. The flexible hollow core coaxial catheter as set forth in claim 21 including an insulating member for circumscribing said second conductor.

23. The flexible hollow core coaxial catheter as set forth in claim 18 wherein the probe comprises an inflatable balloon.

24. The flexible hollow core coaxial catheter as set forth in claim 23 wherein said balloon includes ohmically resistive material interconnected between said first and second conductors for developing a source of heat in response to transmission of RF energy.

25. The flexible hollow core coaxial catheter as set forth in claim 24 wherein said balloon includes a selectively expandable surface to bear against the arterial plaque and wherein said ohmically resistive material is disposed upon said surface.

26. The flexible hollow core coaxial catheter as set forth in claim 25 including means for inflating said balloon to expand said surface to a predetermined expanded state.

27. The flexible hollow core coaxial catheter as set forth in claim 26 including a lumen for conveying a fluid to and from said balloon to inflate and deflate, respectively, said balloon.

28. The flexible hollow core coaxial catheter as set forth in claim 23 wherein said balloon is expandable to a fixed predetermined shape.

29. The flexible hollow core coaxial catheter as set forth in claim 28 wherein said balloon includes an envelope of flexible and essentially inelastic material.

30. The flexible hollow core coaxial catheter as set forth in claim 18 wherein said first conductor comprises a layer of deposited electrically conductive material.

31. The flexible hollow core coaxial catheter as set forth in claim 18 wherein said second conductor comprises a layer of deposited electrically conductive material.

32. The flexible hollow core coaxial catheter as set forth in claim 31 wherein said first conductor comprises a layer of deposited electrically conductive material.

33. The flexible hollow core coaxial catheter as set forth in claim 18 wherein said first conductor comprises a ribbon of electrically conductive material.

34. The flexible hollow core coaxial catheter as set forth in claim 18 wherein said second conductor comprises a further ribbon of electrically conductive material.

35. The flexible hollow core coaxial catheter as set forth in claim 34 wherein said first conductor comprises a ribbon of electrically conductive material.

36. The flexible hollow core coaxial catheter as set forth in claim 33 wherein said ribbon is spirally wound interior of said dielectric member.

37. The flexible hollow core coaxial catheter as set forth in claim 34 wherein said further ribbon is spirally wound exterior of said dielectric member.

38. The flexible hollow core coaxial catheter as set forth in claim 18 including a guide wire disposed within said bore for guiding the catheter into place during the angioplasty procedure.

39. The flexible hollow core coaxial catheter as set forth in claim 18 wherein the cross sectional area of said hollow core coaxial catheter is not more than 0.0007 square inches.

40. The flexible hollow core coaxial catheter as set forth in claim 18 wherein the cross sectional area of said hollow core coaxial catheter is not more than 0.0003 square inches.

41. The flexible hollow core coaxial catheter as set forth in claim 23 including a lumen for conveying a fluid to and from said balloon to inflate and deflate, respectively, said balloon.

42. The flexible hollow core coaxial catheter as set forth in claim 41 wherein said lumen is disposed exterior of said second electrical conductor.

43. The flexible hollow core coaxial catheter as set forth in claim 41 wherein said lumen is disposed within said bore and including means for providing fluid communication between said lumen and said balloon.

44. The flexible hollow core coaxial catheter as set forth in claim 18 including a guide wire housed within said bore for guiding said catheter during the angioplasty procedure.

45. The flexible hollow core coaxial catheter as set forth in claim 18 including means for imaging the vascular site, said imaging means being housed within said bore.

46. The flexible hollow core coaxial catheter as set forth in claim 18 wherein said imaging means comprises a fiber optic and means for illuminating the area to be imaged.

47. An RF heated probe for expanding heated arterial plaque at a vascular site during an angioplasty procedure, said probe comprising in combination:
  (a) an expandable envelope, said envelope including flexible and essentially inelastic material for defining a predetermined shape of said envelope upon expansion of said balloon;
  (b) means for conveying fluid to and from said envelope to expand and contract, respectively, said envelope;
  (c) an ohmically resistive load disposed upon said envelope for heating the arterial plaque proximate said balloon in response to application of RF energy during the angioplasty procedure; and
  (d) means for transmitting RF energy to said ohmically resistive load, said transmitting means including a hollow core coaxial member.

48. The RF heated probe as set forth in claim 47 wherein said transmitting means comprises a catheter having first and second coaxial conductors for transmitting RF energy to said ohmically resistive load.

49. The RF heated probe as set forth in claim 48 wherein said catheter includes a hollow core.

50. The RF heated probe as set forth in claim 48 wherein said catheter includes said conveying means.

51. The RF heated probe as set forth in claim 48 including means for interconnecting said ohmically resistive load with said first and second conductors.

52. An RF heated probe for expanding heated arterial plaque at a vascular site during an angioplasty procedure, said probe comprising in combination:
  (a) an expandable envelope, said envelope including flexible and essentially inelastic material for defining a predetermined shape of said envelope upon expansion of said envelope;
  (b) means for conveying fluid to and from said envelope to expand and contract, respectively, said envelope;

(c) an ohmically resistive load disposed upon said envelope for heating the arterial plaque proximate said envelope in response to application of RF energy during the angioplasty procedure;

(d) means for transmitting RF energy to said ohmically resistive load, said transmitting means comprising a catheter having first and second coaxial conductors for transmitting RF energy to said ohmically resistive load;

(e) means for interconnecting said ohmically resistive load with said first and second conductors; and (f) said envelope including a distal end and a proximal end and wherein the distal end of said ohmically resistive load is electrically connected with said first conductor and the proximal end of said ohmically resistive load is electrically connected with said second conductor.

53. The RF heated probe as set forth in claim 52 including means for electrically insulating said ohmically resistive load from the arterial plaque during an angioplasty procedure.

54. The RF heated probe as set forth in claim 49 including a guide wire housed within said hollow core for guiding said catheter during the angioplasty procedure.

55. The RF heated probe as set forth in claim 49 including means for imaging the vascular site, said imaging means being housed within said hollow core.

56. The RF heated probe as set forth in claim 55 wherein said imaging means comprises a fiber optic and means for illuminating the area to be imaged.

57. The RF heated probe as set forth in claim 49 wherein said conveying means is disposed within said hollow core.

58. The RF heated probe as set forth in claim 57 wherein said conveying means comprises a lumen and including means for establishing fluid communication between said lumen and said envelope.

59. A flexible hollow core coaxial catheter for transmitting RF energy from a source of RF energy to an arterial plaque heating probe, said catheter comprising in combination:

(a) a first electrical conductor for conducting RF energy;

(b) a bore circumscribed by said first conductor;

(c) a second electrical conductor for conducting RF energy;

(d) a dielectric member disposed intermediate said first and second conductors circumscribed by said second conductor and circumscribing said first conductor for impeding flow of RF energy between said first and second conductors;

(e) means for electrically interconnecting the probe between said first and second conductors to heat the probe upon transmission of RF energy from the source of RF energy through said first and second conductors to the probe; and (f) an insulating member for circumscribing said second conductor and a further insulating member for inscribing said first conductor.

60. A flexible hollow core coaxial catheter for transmitting RF energy from a source of RF energy to an arterial plaque heating probe, said catheter comprising in combination:

(a) a first electrical conductor comprising a ribbon of electrically conductive material for conducting RF energy;

(b) a bore disposed radially inwardly of said first conductor;

(c) a second electrical conductor comprising a further ribbon of electrically conductive material for conducting RF energy;

(d) each of said ribbon and said further ribbon includes a core of inelastic dielectric material;

(e) a dielectric member disposed intermediate said first and second conductors for impeding flow of RF energy between said first and second conductors; and (f) means for electrically interconnecting the probe between said first and second conductors to heat the probe upon transmission of RF energy from the source of RF energy through said first and second conductors to the probe.

61. A flexible hollow core coaxial catheter for transmitting RF energy from a source of RF energy to an arterial plaque heating probe, said catheter comprising in combination:

(a) a first electrical conductor comprising a ribbon of electrically conductive material for conducting RF energy;

(b) a bore disposed radially inwardly of said first conductor;

(c) an electrically insulating layer for defining said bore and wherein said ribbon is spirally wound about said layer;

(d) a second electrical conductor for conducting RF energy;

(e) a dielectric member disposed intermediate said first and second conductors for impeding flow of RF energy between said first and second conductors; and (f) means for electrically interconnecting the probe between said first and second conductors to heat the probe upon transmission of RF energy from the source of RF energy through said first and second conductors to the probe.

62. The flexible hollow core coaxial catheter as set forth in claim 61 wherein said second conductor comprises a further ribbon of electrically conductive material and wherein said further ribbon is spirally wound about said dielectric member.

* * * * *